United States Patent [19]

Rowley et al.

[11] Patent Number: 4,975,532

[45] Date of Patent: Dec. 4, 1990

[54] METHOD TO DERIVATIZE DEXTRAN

[75] Inventors: Gerald L. Rowley, San Jose; Larry R. Hillis, Milpitas, both of Calif.

[73] Assignee: Sclavo, Inc., Sunnyvale, Calif.

[21] Appl. No.: 137,986

[22] Filed: Dec. 24, 1987

Related U.S. Application Data

[63] Continuation-in-part of Ser. No. 935,952, Nov. 28, 1986.

[51] Int. Cl.$^5$ .............................................. C08B 37/02
[52] U.S. Cl. ...................................... 536/51; 536/112; 436/529; 514/59
[58] Field of Search .................. 536/51, 112; 436/529; 514/59

[56] References Cited

U.S. PATENT DOCUMENTS

| | | | |
|---|---|---|---|
| 3,853,987 | 12/1974 | Dreyer | 424/1 |
| 4,081,244 | 3/1978 | Polito et al. | 436/529 |
| 4,119,521 | 10/1978 | Chirikjian | 536/112 |
| 4,175,073 | 11/1979 | Carlsson et al. | 536/112 |
| 4,231,999 | 11/1980 | Carlsson et al. | 424/1 |
| 4,232,119 | 11/1980 | Carlsson et al. | 435/7 |
| 4,298,395 | 11/1981 | Hildebrand et al. | 536/112 |
| 4,298,593 | 11/1981 | Ling | 424/1 |
| 4,303,786 | 12/1981 | Goldstein et al. | 536/51 |
| 4,423,143 | 12/1983 | Rubenstein et al. | 435/7 |
| 4,429,008 | 1/1984 | Martin et al. | 436/532 |
| 4,508,892 | 4/1985 | Yoshida | 536/51 |
| 4,560,648 | 12/1985 | Armenta | 435/7 |
| 4,576,912 | 3/1986 | Yaverbaum et al. | 436/529 |
| 4,595,656 | 6/1986 | Allen | 435/7 |
| 4,675,392 | 6/1987 | Dahmen et al. | 536/17.2 |
| 4,757,141 | 7/1988 | Fung et al. | 536/112 |
| 4,774,191 | 9/1988 | Khanna et al. | 436/529 |
| 4,801,504 | 1/1989 | Burdick et al. | 436/529 |

FOREIGN PATENT DOCUMENTS 0077671 10/1982 European Pat. Off. .
0155224 3/1983 European Pat. Off. .
8404970 12/1984 PCT Int'l Appl. .

OTHER PUBLICATIONS

Watanabe et al., (1979) Clin. Chem. 25(1):80–82.
Ishikawa et al., (1983) Journal of Immunoassay 43(3):209–327.
Smith et al., (1981) Ann. Clin. Biochem. 10:253–274.
Jansen et al., (1982) Immunological Rev. 62:185–216.
Nilsson et al; Biochem. Biophys. Res. Commun. 102(1):449–457, Sep. 16, 1981.
Yalpani et al; J. Polymer Sci.: Polym. Chem. Ed. 23:1395–1405 (1985).
Mandenius et al; Analytical Biochem. 157:283–288, Sep. 1986.
Wiedmann et al.; Biol. Chem. Hoppe-Seyler's 367(Suppl.):208 Ab. 18.02.13 (1986).
Wikström et al; J. Chromatog. 388:123–134 (1987).
Persson et al; J. Chromatog. 457:183–193 (1988).

*Primary Examiner*—Ronald W. Griffin
*Assistant Examiner*—Nancy S. Carson
*Attorney, Agent, or Firm*—Irell & Manella

[57] ABSTRACT

A method to convert the hydroxyl groups of solubilized dextran to the tresylate forms which can be displaced by a nucleophile is disclosed. The method of the invention requires the reaction of dextran with the tresylating reagent in the presence of dry DMSO. The resulting tresylate can be converted to labeled dextrans which have direct linkages of a nucleophilic label to the carbons of the dextran backbone.

2 Claims, 5 Drawing Sheets

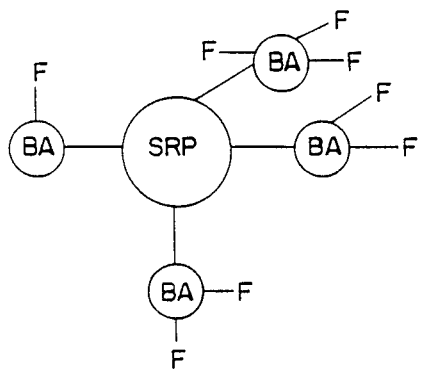
FIG. IA
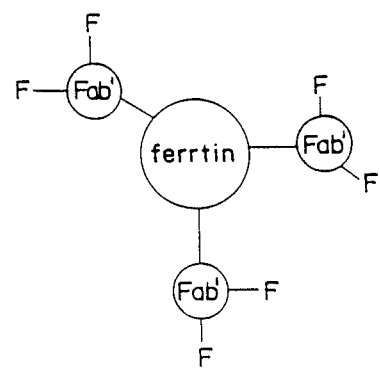
FIG. IB
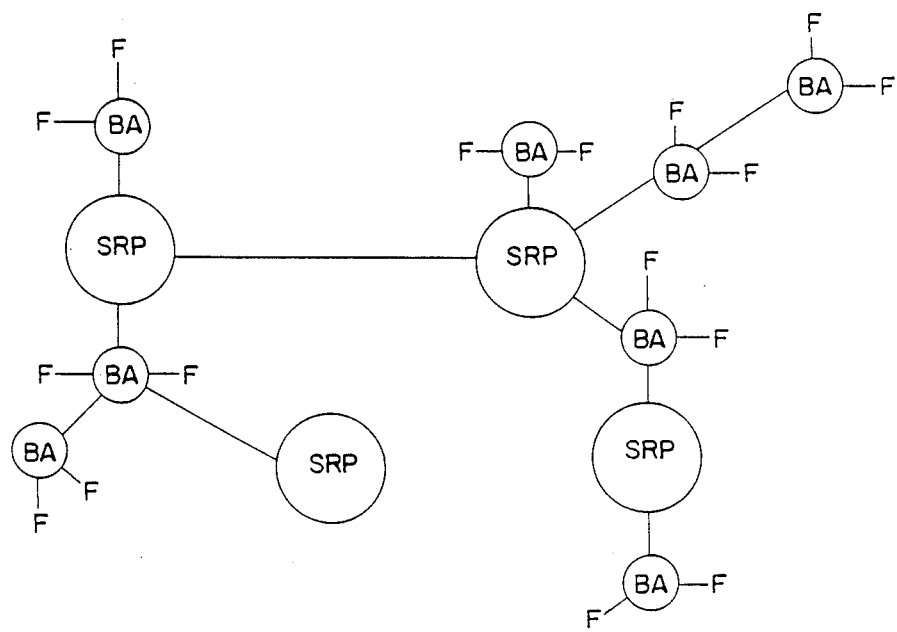
FIG. IC

METHOD TO DERIVATIZE DEXTRAN

RELATIONSHIP TO OTHER APPLICATIONS

This is a continuation-in-part of U.S. patent application Ser. No. 935,952, filed Nov. 28, 1986, now pending.

FIELD OF THE INVENTION

The invention relates to the determination of substances in biological or other samples using a binding assay, such as immunoassay, with labeled reagents. More particularly, it relates to a new design for labeled reagents which participate in the binding reaction in such assays. The general concepts involved in this design are illustrated by assays for T3, IgE, ferritin, and TSH.

BACKGROUND OF THE INVENTION

Techniques and protocols for assays involving immunoreaction of antigen/immunoglobulin moieties or other specifically binding moieties have been known for almost thirty years. One of the earliest disclosures of such protocols was the original radioimmunoassay procedure of Yalow. There are hundreds of specific assays and dozens of general protocols involved in such assays, whose unifying feature is that their specificity depends on the ability of the analyte in question, but not the contaminants accompanying it in the sample, to bind to the reagent.

Most frequently, the specific binding is an antigen/antibody immunoreaction and its variants, including the use of derivatives of immunoglobulins to bind to an antigen. The antigen, itself, may also, of course, be an immunoglobulin. Other examples of specific binding, while perhaps less common, are nevertheless important, including the highly specific reaction between avidin and biotin, the attraction of particular lectins for certain proteins or glycoproteins, and so forth. The specificity need not be exquisite, as long as there are no interfering substances present in the sample which also bind to the reagent.

In broadest concept, the specific binding assays to which the designed reagents of the invention are applicable are conducted either in a direct or competitive manner. In a direct assay, the specific reagent is either itself labeled or provided a mechanism to acquire a label and used to bind to the analyte in the sample, thus removing it from the physical environment of the contaminants, or in some way changing its environment so that only its presence, among the associated materials in the mixture, is detectable. The amount of label associated with the analyte is then a direct measure of the quantity of analyte in the sample. Often a labeled antibody is employed for direct assays, in which case the assay is generally termed "immunometric".

Conversely, in the competitive approach, the analyte is caused to compete with itself in labeled form for the same specific reagent. The higher the concentration of competing analyte in the solution, the less label will be bound to the specific reagent. Thus, the amount of label associated with the specific reagent/analyte complex is in inverse proportion to the amount of analyte in solution.

The foregoing methods can be conducted as solid-phase assays, including sandwich assays, and may involve more than one specifically interacting substance in forming the final labeled conjugate.

Over the more than twenty years that this assay approach has been used, a number of labeling systems have come into common use, depending on the nature of the analyte, and the sensitivity required. The most common labels are radioisotopes, fluorescent materials, or enzymes capable of catalyzing detectable reactions. Radioimmunoassay (RIA), which employs radioisotopes as labels, generally is quite sensitive but, of course, is cumbersome to conduct due to the dangers associated with handling radioisotopes and the equipment involved in quantifying the radiation. Fluorescent labeling has been moderately less sensitive, a problem which might be overcome by increasing the number of dye molecules used as label, were it not for crowding effects resulting in the quenching of fluorescence due to the proximities of the fluorophores. Enzyme-mediated immunoassay techniques are also limited in sensitivity by the number of labeling enzyme molecules which can be crowded onto the specific reagent. The problem of fluorescence quenching with multiple labels is serious enough to diminish the sensitivity of assays using this approach. Concentration quenching with multiple labels is discussed in, for example, Smith, D. S., et al, *Ann Clin Biochem* (1981) 18:253. Thus, it would be desirable to utilize a method of labeling which permits enhancement of sensitivity by permitting multiple labels, which still retain their effectiveness, to be attached to the specific reagent. The present invention, by designing a method and final product to achieve efficient multiple labeling, provides the opportunity to maximize the practicality of labeled specific analytical binding reactions.

DISCLOSURE OF THE INVENTION

The invention relates to techniques for labeling specific reagents useful in analytical applications and to the resulting labeled reagents. The design permits the use of a multiplicity of label in association with a single molecule of specific reagent without the disadvantages normally encountered in directly labeling such reagents with more than one or several labeling entities. In particular, the problem of fluorescence quenching is overcome.

In one design, the specific reagent, which might be, for example, an antigen or antibody, is provided with a multiplicity of bulking groups which contain only one site capable of forming the linkage to join them to the reagent. The bulking agent moieties have one or more labels covalently attached.

Thus, in one aspect, the invention relates to specific binding reagents having a binding moiety conjugated to at least one, preferably a multiplicity of, bulking agents, to which, in turn, are bound one or more labeling groups. In other aspects, the invention relates to methods to prepare the reagents of the invention and to methods to analyze samples employing them.

BRIEF DESCRIPTION OF THE DRAWINGS

FIG. 1A shows a diagram of a preferred generic design of the reagent of the invention; FIG. 1B shows an embodiment using ferritin as specific reaction partner, FIG. 1C shows a less preferred randomly bonded form.

MODES OF CARRYING OUT THE INVENTION

A. Definitions

Figure 2A:
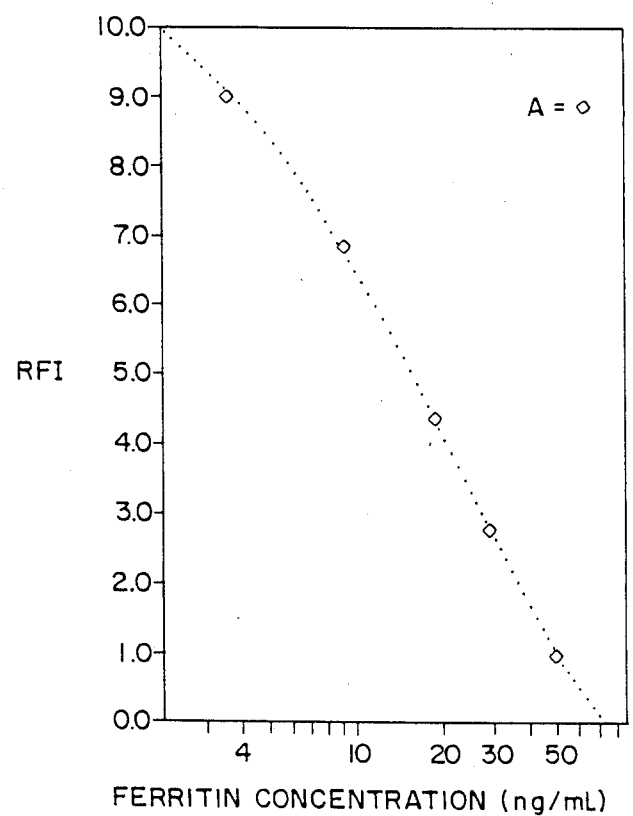
FIG. 2A shows the results of quantitation of ferritin calibration standards using the method of the invention.

As used herein, "substance specifically reactive with analyte" refers to a substance which is capable of reacting with whatever comprises the analyte, but not with contaminants under the conditions of the assay. This substance is most commonly a component of an antigen-/antibody reaction; it can either be the antigen or the antibody. The immunospecific substance may be either a complete immunoglobulin or antibody specific for the antigen, or may be an "immunospecific portion thereof", such as the F(ab')$_2$ fragment, or other portion of the antibody that reacts specifically with antigen. The antigen can be any of a variety of materials, including immunoglobulin or fragments thereof. It may be a protein, a carbohydrate, or any molecule of sufficient size to constitute an antigenic determinant. Antibodies, in general, can be raised against sites of approximately 10 Å or more if the materials comprising such sites are sufficiently large or are made sufficiently large to be immunogenic by conjugation to carrier molecules. This is frequently the practice in generating antibodies to, for example, smaller peptide units or other small molecules in specific vaccines.

The "substance specifically reactive with analyte" also refers to the components of reactions which are not immunoreactions, but which retain the property of specificity in the face of contaminants. For example, certain lectins react specifically with the carbohydrate moieties on certain proteins, certain receptors found on cell surfaces react specifically with their target materials; biotin reacts specifically with avidin. Thus, "substance specifically reactive with analyte" is used as a general term to indicate the other partner in an affinity reaction between an analyte substance and a substance specifically reactive with it, including, but not limited to, antibody and a material containing an antigenic determinant for which it is specific.

More general than a "substance specifically reactive with analyte" is a "specific reaction partner" (SRP) which term may refer either to the above substance reactive with analyte or to the analyte itself. Each is the counterpart of the other in the highly specific interaction which forms the basis for the assay.

Also, the term "specific reaction partner" refers to the substance accounting for the specificity pATENT in either labeled or unlabeled form, as will be clear from the context.

One SRP "complementary" to another refers to the two members of the specifically reacting pair. Thus, an SRP complementary to an analyte refers to a moiety which specifically reacts with the analyte; a SRP complementary to an SRP contained in the reagents of the invention is specifically reactive therewith.

"Label" (L) refers to a moiety which accounts for the detectability of a complex or reagent. In general, the most common types of labels are fluorophores, chromophores, radioactive isotopes, and enzymes.

"Antibody" is defined conventionally, but also includes fragments thereof, such as Fab or F(ab')$_2$ fragments, which retain the specificity.

"Fluorophore" (F) refers to a substance or portion thereof which is capable of exhibiting fluorescence in the detectable range. Typically, this fluorescence is in the visible region, and there are common techniques for its quantitation. Examples of fluorophores which are commonly used include fluorescein, (usually supplied as fluorescein isothiocyanate [FITC]), rhodamine, dansyl, and umbelliferone.

"Bulking agents" (BA) refer to molecules which are not themselves specific with regard to the participants in a reaction specific for analyte, but which are molecules of sufficient size that they can effectively be used as bulky linkers between specific portions of the reagent and the label. Depending on the specific components of the reaction, the workable size for the bulking agents can vary widely. However, in general, for most applications, the bulking agents of the invention should have a molecular weight on the order of 1–2000 kd, preferably 20–100 kd. These sizes cover the majority of cases, and represent the most generally useful range. However, no definite outer limits can be set, and in any particular instance smaller or larger bulking agents than those here suggested may be desirable. In order to be operable in the preferred method of the invention for preparation of the labeled reagent, the bulking agent should have only one functional group which is reactive with a particular functional group on a heterobifunctional linker. Particularly preferred is a sulfhydryl group.

As illustrated below, a particularly useful bulking agent is an Fab' fragment of rabbit IgG, since not only is this of an approximately correct molecular weight, but it also contains one and only one sulfhydryl group, which can then be used to bind specifically to heterobifunctional linkers designed to form thioethers or disulfide linkages.

Also particularly useful as a bulking agent is dextran. "Tresylated dextran" refers to a dextran composition in which a substantial number of hydroxyls have been converted to substituents of the formula—$OSO_2CH_2CF_3$, which is a good leaving group, replaceable by label. "Fluoresceinated dextran" refers to a dextran composition in which a substantial number of hydroxyls have been converted to substituents containing a fluorescein nucleus.

"Derivatized or protected dextran" refers to a dextran in which the single aldehyde (hemiacetal) group has been reacted with a derivatizing or protecting group. By "protecting group" is meant a moiety which is removable subsequent to a reaction in which the protecting group serves that purpose. For example, in the illustration below, tresylation would preferably occur at the aldehyde (hemiacetal) and in order to insure reactivity of the hydroxyl groups whose reaction is desired, the aldehyde (hemiacetal) must be protected by addition of a suitable substituent. However, this substituent can subsequently be removed. "Derivatized" dextran refers to dextrans wherein the aldehyde (hemiacetal) has been converted to a different functional group, or an additional moiety has been reacted with it, which is not necessarily removable subsequent to an intermediate reaction. In general, the derivatized dextrans employed hereinbelow retain their derivatization in order to employ the derivative group in coupling to a specific reaction partner.

B. General Description of Preferred Embodiments of the Invention

In general, the preferred compositions of the invention have the configuration shown in FIG. 1 both in the general and for the particular case of ferritin and other exemplified SRPs. In this design, the specific reaction partner is linked to a multiplicity of bulking agents. The bulking agent in turn is linked to one or more labels. The ratio of bulking agent to specific reaction partner is variable, and to some extent depends upon the analyte being tested. For labeling of specific reaction partners which are relatively low in molecular weight, such as T3, only one bulking agent per reagent molecule may suffice. In this case, presence of the bulking agent prevents the fluorophore label from being in the proximity of the iodide moiety of T3; iodide is a known quencher. However, for larger reagents, more bulking agent may be used to increase sensitivity. The upper limit also depends, of course, on the size of the specific reaction partner. For example, for fluorescent labeling of ferritin, an advantageous range is approximately 5–14, the lower limit being set to assure sufficient sensitivity and the upper limit being set to prevent unacceptable overcrowding of the label.

Appropriate and preferred procedures to put together a reagent of the type shown in FIG. 1 are described below. In order for these preferred procedures to be effective, the bulking agent must contain only one functional group capable of reacting with linker, and a heterobifunctional linker is required, or, if appropriate, a unique functional group may be reacted directly with the SRP. If dextran is used as a bulking agent, the carbon representing the sole aldehyde (hemiacetal) functional group constitutes a unique functional group and can be used to react with linker or can be modified to react directly with the SRP.

The bulking agent either per se or in protected or derivatized form, is first labeled with the desired labeling material by a convenient chemical reaction appropriate to the choice of components. For example, the amino groups of a protein bulking agent may be used to bind with the commonly used fluorescent compound fluorescein isothiocyanate (FITC); the hydroxyls of a carbohydrate bulking agent can be used to attach to label. The stoichiometry of label to bulking agent can be, in part, controlled by the relative amounts of materials added to the reaction mixture. The resulting labeled bulking agent or derivatized BA is then linked, optionally through a heterobifunctional linker, to the specific reaction partner.

Linkage through a bifunctional linker can be achieved in two alternative ways. The linker can be put first on the specific reaction partner (SRP) after protecting or blocking, if necessary, alternate groups which would react with the other end of the bifunctional linker. Alternatively, the linker is first bound to the labeled bulking agent, again preliminarily protecting or blocking any groups on the bulking agent, which would otherwise react with the other functional group on the linker. The SRP or bulking agent (BA) bearing the linker is then conjugated to its opposite member, taking advantage of the reactivity of the other group on the linker.

In one specific illustration, the heterobifunctional linker contains sulfhydryl-binding functional groups at one end, for reaction with a protein bulking agent, such as rabbit IgG Fab' fragment containing only one sulfhydryl group and a labile group at the other, such as an active ester. This set of functional groups mandates a certain sequence of reactions to link the bulking agent to SRP. For example, a frequently used linker, sulfo-SMCC, contains a highly labile ester reactive with the amino groups of a protein substrate as one functional group and the sulfhydryl-binding group as the other. The ester groups must be reacted with protein substrate first. This is in order to prevent hydrolysis and inactivation of the functional group during reaction with the opposite, sulfhydryl-reacting end of the molecule. Accordingly, in this case, the linker is first linked to SRP by virtue of the labile ester linkage, having first protected the sulfhydryl groups of SRP, if necessary, using, for example, iodoacetate or N-ethylmaleimide (NEM), as illustrated below. The SRP-containing linker is then reacted with the single sulfhydryl group on the Fab' fragment to complete the reagent.

However, this sequence is mandated only by the specific nature of the functional groups on the heterobifunctional linker. Should a linker have been used having, for example, instead of an N-hydroxysuccinimide ester (active ester) group for reaction with the amino side chains, an azide functional group, which requires activation by light in order to become reactive, the linker could have been bound to the bulking agent through the sulfhydryl linkage first, and then the linker-modified bulking agent used to react with the SRP.

In addition, if the nature of the chemistry of the unique functional group contained in the bulking agent permits, conjugation may be made directly to the SRP. For a peptide bulking agent, for example, which contains only a single side chain carboxylic or amino residue, direct conjugation to the SRP through a dehydrating agent mediated reaction can be had. When the bulking agent is dextran, as set forth below, the unique aldehyde moiety can be used directly, or preferably converted to an alternate unique functional group which can be used either for direct binding to the SRP, or which can be conjugated to the SRP through an appropriate heterobifunctional linker.

There are other cases in which linkers are not required also. A bulking agent containing a single —SH group could be "activated" with a sulfhydryl activating agent—e.g., by reaction with 5,5'-dithiobis-(2-nitrobenzoic acid)—to obtain a reactive disulfide capable of binding to available —SH groups in the SRP.

Thus, in another preferred embodiment, in which a carbohydrate, such as dextran, is used as bulking agent, the label, such as a fluorophore, can be bound by converting a suitable number of the hydroxyl groups to leaving groups displaceable by a nucleophile. Reaction of the protected or derivatized dextran with tresyl chloride ($CF_3CH_2SO_2Cl$) can be used for this conversion. The analogous reaction with Sepharose is known and is conducted in dry acetone with a pyridine catalyst (Nilsson, K., et al *Meth Enzymol* (1984) 104:156); these conditions appear disadvantageous in the case of dextran, but it has been found that the conversion proceeds smoothly when the solution of tresyl chloride is added to a solution of derivatized or protected dextran in dry DMSO with a pyridine catalyst. Dextran, having, for example, an attached sulfhydryl linker function can also be used as a substrate.

If the label is to be attached by replacement of tresyl chloride, the tresylation and replacement of tresyl groups must be conducted with the dextran in the derivatized or protected form, otherwise the tresyl moiety appears to react preferentially with the hemiacetal functional group. The aldehyde can either be protected during the tresylation and labeling reactions and subsequently deprotected thus freeing the aldehyde for conversion to a group suitable for binding to the SRP (through a linker or not) or the dextran may be derivatized in a manner which can be subsequently employed for SRP conjugation.

For example, the aldehyde can be protected by reaction with diethyl hydrazine to obtain the dextran hydrazone, which can then be tresylated and labeled, for example, by fluoroscein moieties. Subsequent deprotection is with an excess of pyruvic acid to obtain the labeled unprotected dextran. Another approach is conversion of the dextran to the corresponding amine by reaction of ammonia in the presence of sodium cyanoborohydride. The resulting amine must, itself, be protected, for example, by derivatizing the amino group to form the t-butyloxycarbonyl (BOC) derivative and the BOC-protected amine is then tresylated and labeled, with subsequent deprotection using trifluoroacetic acid. The deprotected amine can then be used for conjugation to the SRP through, for example, the use of heterobifunctional linker such as sulfo-SMCC, as described below.

Thus, the dextran can be prepared or partially prepared for conjugation to the SRP before labeling, or the aldehyde group may simply be protected during the labeling process and subsequently freed for subsequent reaction.

By adjustment of the ratio of tresyl chloride to dextran, a desired number of hydroxyls per dextran are converted to the form $-OSO_2CH_2CF_3$. The reaction is conducted under a dry atmosphere and suitable conditions include ambient temperature for 2–72 hours; the molar ratio of tresyl chloride reagent to dextran substrate can vary from 500:1 to 10:1. A workable range of temperatures includes temperatures from the freezing point of DMSO to about 100° C.; higher temperatures in this range (above 50° C.) are less preferred. Times for reaction depend on temperature and can thus be from several minutes to about a week.

The product tresylated dextran can be recovered and purified, but this is difficult and unnecessary, or the reaction mixture can be used directly for reaction with label. The nucleophilic group attached to label may generally be —OH, which is not favored or, much more preferably —SH or —NH—; other groups of comparable nucleophilicity may be substituted. It is understood that OH is much less nucleophilic, which accounts for the result that extensive intramolecular crosslinking does not occur. The labeled products so produced are different in composition and structure from commercially synthesized labeled dextrans which conjugate to label using the nucleophilicity of the dextran hydroxyl oxygens.

In one embodiment, the label may be a fluorescein derivative, such as Fl—NHCOCH$_2$SH, or commercially available fluoroscein substituted alkyl amines. For Fl-NHCOCH$_2$SH, displacement of the tresyl groups can be conducted in aqueous buffer, pH 7-10, preferably about 8.5, at about ambient temperature while the derivatized dextran solution is added dropwise. The resulting labeled dextran then is recovered from the reaction mixture by addition of acid in ethanol and centrifugation.

Thus, for example, the resulting fluorescein dextran derivative is linked to the dextran through —SCH$_2$CONH—Fl; dextran conventionally derivatized using FITC has linkages of the form: dextran-OCSNHFl.

Using dextran of MW about 70 kd, 5–11 fluorescein moieties per dextran can be conjugated, resulting in a quantum efficiency of 0.4–0.6, comparable to that of Fab' labeled with 5-((((2-carboxyethyl)-thio)acetyl-)amino) fluorescein.

In general, the ratio of label to dextran is dependent on molecular weight, as further set forth below. For the approximately 70 kd dextran discussed above, a suitable range for label is 5–11 label molecules per dextran. For lower molecular weight, such as 2 kd, as few as one label per molecule may be desirable; for higher molecular weights such as 2,000 kd, as many as 300. For the intermediate tresylated form, however, the ratio of tresyl groups to dextran must be at least as great as the desired label to dextran ratio and may advantageously be made higher, as much as 10 times higher in view of the hydrolysis side reaction which often accompanies the displacement of the tresyl groups by the nucleophile derivatized label. Thus, using the foregoing example for a 70 kd dextran, ratios of tresyl group to dextran should be of the order of 10:1 to 100:1.

The labeled bulking agent can then be linked to the SRP using a number of strategies employing the single aldehyde at the foot of the dextran; for example, utilizing a hydrazone linkage with an acyl hydrazide derived from carboxyl or amide groups on the SRP, or through an oxime linkage to O-alkyl hydroxylamine linkers attached to proteinaceous SRPs. In one convenient protocol, the aldehyde is converted to the amine by reaction with NH$_3$ in the presence of CNBH$_3$, and the resultant —CH$_2$NH$_2$ reacted directly to the carboxyl side chains of the SRP by simple dehydration in the presence of carbodiimide reagents, such as DCC. In addition, a large number of linking agents are available commercially which permit increased specificity. For example, N-succinimidyl 3-(2-pyridyldithio) propionate (SPDP) and 4-(N-maleimidomethyl)cyclo-hexane-1-carboxylate (SMCC), available from Pierce Chemical Co. can be used. For SPDP, the dextran derivative is reacted first using conditions described by the manufacturer to displace the succinimidyl moiety, and then the dextran/linker conjugate conjugated to available sulfhydryl groups on the SRP. If the SRP does not contain sulfhydryl, alternate linkers are chosen compatible with the available functional groups. The number of labeled dextrans per SRP is varied according to the available linking groups on the SRP and the fluorescence level desired. Typical ratios of labeled BA/SRP are 1:1 to 10:1.

If the appropriate linker using a sulfhydryl moiety is employed, the dextran/linker intermediate can be converted to the free sulfhydryl for analysis by reaction in a reducing agent such as dithiothreitol. In a typical preparation, analysis shows about 0.7 SH groups per dextran, and a quantum efficiency for 5–11 fluorescein per dextran of 0.4–0.6, as noted above.

Although heterobifunctional linkers or direct conjugation are preferred, homobifunctional linkers and permissive reaction stoichiometries can be used to obtain composites which are less clean, but nevertheless workable, forms of the reagents of the invention. Complexes wherein bonds between individual BA molecules exist, or wherein a BA molecule is linked to more than one SRP, can also be used in some cases and may exhibit decreased quenching. Such a "random" configuration is shown in FIG. 1C. In such cases, also, a dehydrating agent, such as a carbodiimide, e.g. ethyl carbodiimide or dicyclohexyl carbodiimide, can be used to obtain an amide bond linking the BA directly to the SRP.

In any case, the SRP-((BA)$L_n$)$_m$ (where L is the label) is a multiply labeled moiety providing high sensitivity in a variety of specific binding assays. If fluorescent label is used, fluorescence quenching between the large number of fluorophores is minimized by the spacing provided by the dextran. In general, cross-label interference is prevented, and the effective volume occupied by the SRP is increased. The values of n and m are variable, depending on the nature of the components, but, in general, n is 1-20, and m is 1-10. For high molecular weight dextran, n can be much higher-e.g., 300:1.

C. The Components of the Reagent Compositions

The nature of the various components of the compositions of the invention depends, of course, on the analyte and on the protocol selected. If a competition assay is to be run, the SRP to be labeled according to the method of the invention corresponds to, i.e., is equivalent to or is the same compound as the analyte itself. If noncompetitive, immunometric assay methods are to be used, the labeled SRP is either itself directly reactive with the analyte or reactive with an intermediate material which is specifically reactive with the analyte.

Thus, for competition reaction, suitable SRP moieties include analytes commonly assessed in biological fluids, such as, for example, any of a variety of enzymes, including G-6-P, alkaline phosphatase, hexokinase, catalase, alcohol dehydrogenase, and so forth; various hormones, such as luteinizing hormone, follicle-stimulating hormone, thyroid-stimulating hormone (TSH), human chorionic gonadotropin, thyroxin derivatives (T3 and T4), ferritin, α-fetoprotein, prolactin, and LH, particular immunoglobulins, such as IgE; small molecules such as theophylline, diazepam, penicillin, and tetracycline, against which antibodies could be raised; biotin; legal or illegal drugs; virus proteins; and so forth.

If the protocol is that of a noncompetitive (direct) assay, the SRP might well be an antibody or portion thereof specifically reactive with any of the analytes such as those listed above, or the specific reaction partner may be reactive simply with another intermediate specific reaction partner. For example, if the protocol is designed to detect the presence of human chorionic gonadotropin (hCG) using mouse antibodies specific against hCG as a primary reagent, the labeled reagent might be, for example, rabbit anti-mouse IgG.

The bulking agent is, generally, a polymer of molecular weight of at least approximately 1 kd, and an upper limit which depends on the size of the SRP and the number of bulking agents intended to be crowded around the specific reagent portion of the finished composition. Of course, if the size of the BA compared to the SRP is too large, the number of BA which can be attached without overcrowding is quite limited. In order to provide for efficient preparation, the bulking agent should contain only one functional group capable of reacting with a particular functional group on the end of a heterobifunctional linker. For example, proteins containing only one side-chain amino group might be used, or a polymer of glycine might be used, provided conjugation to label could be achieved through, for example, the amino or carboxy terminus. Alternatively, polymers providing a limited number of functional groups for binding of label might be used, such as a 10:1 mixture of glycine with cysteine. The SH groups of the cysteine residues could then be used to bind to label, while the attachment to linker is through either terminus, or 10:1 mixture of lysine with cysteine; the amino groups bind to label and —SH to linker. A particularly preferred BA might be polyproline, as it exhibits a singularly stable spacer function.

A particularly convenient bulking agent is the Fab' fragment of, for example, rabbit immunoglobulin, since it contains one sulfhydryl group, a common functional group for reactivity with commercially available bifunctional linkers. This fragment is prepared by means well known in the art by treating immunoglobulin with pepsin, thus yielding the F(ab')$_2$ fragment, followed by treating with reducing agent to reduce the single disulfide bond and thus produce two Fab' portions. Other suitable and preferred peptides which are known to contain only one —SH group include mercaptoalbumin and human α1-antitrypsin. Of course, any protein or peptide containing a single instance of a type of reactive functional group would be suitable.

Another suitable and preferred bulking agent is dextran. Dextran is a highly branched glucose polymer with a single potential reducing group, which can be used directly, converted to an alternate group, and/or attached to linker for binding to the specific reaction partner. The backbone polymer is linked α(1-6) and the branches by α(1-4) glycosidic bonds. The dextran polymer can be thus envisioned to have a tree-like appearance with a single aldehyde at its base. Dextran is available in a range of molecular weights of about 10 kd-2000 kd, and has a multiplicity of hydroxyls available for conjugation, for example, to fluorophores.

Dextran thus has advantageous features as the bulking agent herein. It has a single unique functional group for conjugation to the specific reaction partner, has large numbers of binding sites for label, and its size for a particular assay can be chosen arbitrarily.

Groups suitable for labels are multitudinous and well known in the art. Useful labels containing radioactivity include $I^{131}$, $I^{125}$, $Ce^{137}$, and $P^{32}$. Suitable fluorescent labels include fluorescein, dansyl, rhodamine, Texas Red, eosin, umbelliferone, and cyanine and so forth. Chromophores are less convenient because their detection is less sensitive, but nevertheless are included within the scope of the invention, and include a large variety of compounds known in the art for dyeing fabrics, for example. Suitable enzyme labels include horseradish peroxidase, glucose dehydrogenase, glucose oxidase, and diaphorase. A large number of suitable labels are known to those practicing the art and are readily available to them.

Heterobifunctional (and homobifunctional) linkers are also commercially available and include, generally, those reactive with sulfhydryl groups or amino groups of proteins. Particularly popular are SMCC and SPDP and their water soluble sulfo forms, as explained below. A representative list of functional groups contained in such heterobifunctional linkers includes activated esters, such as imidates, azides, and activated disulfides.

There are a large number of heterobifunctional agents which generate a disulfide link at one functional group end and a peptide link at the other, and these have been used extensively. One of the most popular of these is N-succinimidyl—(2-pyridyldithio) propionate (SPDP). This reagent creates a disulfide linkage between itself and a cysteine residue in one protein and an amide linkage through the amino on a lysine, or other free amino group in the other. A variety of such disulfide/amide forming agents are known. See for example,

*Immun. Rev.* (1982) 62:185. Other bifunctional coupling agents form a thioether rather than a disulfide linkage. Many of these thioether forming agents are commercially available and include reactive esters of 6-maleimidocaproic acid, 2-bromoacetic acid, 2-iodoacetic acid, 4-(N-maleimidomethyl) cyclohexane-1carbolic acid and the like. The carboxyl groups can be activated by combining them with succinimide or 1-hydroxy-2-nitro-4-sulfonic acid, sodium salt. A particularly preferred coupling agent for the method of this invention is succinimidyl 4-(N-maleimidomethyl) cyclohexane-1-carboxylate (SMCC) obtained from Pierce Company, Rockford, Ill. Some of these representative compounds may be rendered water soluble by addition of a hydrophillic group, such as, for example, a salt of sulfonic acid substituent. The foregoing list is not meant to be exhaustive, and modifications of the named compounds can clearly be used.

Other coupling agents that may be used are various bifunctional derivatives of imidoesters such as dimethyl adipimidate HCl, active esters such as disuccinimidyl suberate, aldehydes such as glutaraldehyde, bis-azido compounds such as bis(p-azidobenzoyl)hexanediamine, bis-diazonium derivatives such as bis-(p-diaoziumbenzoyl)-ethylene diamine, diisocyanates such as tolylene 2,6-diisocyanate, and bis-active fluorine compounds such as 1,5-difluoro-2,4-dinitrobenzene.

In a typical, preferred approach, a thioether linkage is formed between a sulfhydryl on the BA portion of the conjugate and the coupling agent and an amide linkage is formed between an $\epsilon$-$NH_2$ of a lysine contained in the SRP and the carboxyl of the coupling agent.

D. Proportion of Components and Properties of the Composition

The compositions of the invention have certain unexpected properties. For example, in many instances, the antigenic reactivity of the SRP in the specific reaction is better preserved in constructing a labeled moiety according to the invention rather than by conventional direct labeling. Loss of reactivity due to labeling is apparently diminished by the use of bulking agent. This appears to be true for T3 as SRP, and there are data below demonstrating this for IgE as SRP.

Since the reagent compositions contain multiple labels on their surface, the sensitivity of the assay is dramatically increased, and increased even over directly labeled SRP with multiple labels. This is because the proximity of the labels, when directly attached, causes fluorescence quenching in the case of a fluorescent label, thus obviating the advantage of increased sensitivity; or, in the case of an enzyme label, negatively impacts the activity of a particular labeling enzyme due to overcrowding. Thus, the reagents constructed according to the method of the invention offer increased effectiveness in the specific reaction binding capability, and also increased sensitivity.

To achieve these ends, the ratio of label to bulking agent and of bulking agent to SRP is clearly important. A few general guidelines as to the optimum proportions can be given, although, of course, the most advantageous proportions are highly dependent on the nature of the components chosen for a particular embodiment.

In general, the proportions are regulated by the considerations set forth hereinabove. For ferritin or for IgE, the preferred ratio of Fab' to SRP is 5-14. Ratios greater than 14 lead to overcrowding and therefore to occultation of binding sites; ratios less than 5, at least in fluorescence assays, lead to reduced sensitivity. For T3 as the SRP, however, because of its small size, a ratio of Fab'/T3 of 1 is preferred.

When fluorescein is used as the label in the IgE, T3, or ferritin assays, ratios of fluorescein/Fab' of 1-6, or preferably 1-4.5, or more preferably 1.5-2.5, are used. The preferred ratios offer the optimum balance between the maximum number of fluorescence molecules and the minimum amount of quenching.

It will be apparent that the number of groups labeling the bulking agent, and the number of bulking agents bound to the SRP are highly dependent on the nature of these groups—on the nature of the SRP and BA especially. For example, for dextran which can be prepared in a wide range of molecular weights from about 2 kd to about 2,000 kd, the larger molecular weight molecules clearly can contain a larger number of labels. Thus, for 2,000 kd dextran, a 300:1 is not unreasonable; for smaller molecular weight forms of this material, smaller ratios, of the order of 2:1 might be employed. A typical ratio of L:BA is 10-30:1.

Similarly, for SRPs which are quite bulky, the number of bound BA molecules is relatively high; for smaller SRPs, even a 1:1 ratio is acceptable.

The method of constructing the compositions described is advantageous in minimizing side reactions. It is, of course, possible to synthesize the compositions of the invention using other protocols, such as employing homobifunctional linkers for the binding of SRP to BA. However, this requires that the particular product mixture which contains the desired composition be isolated from mixtures which will also contain SRP linked to SRP, BA linked to BA, and polymeric mixtures of each and both components.

In addition, of course, some of these may be satisfactory, and separation may not be necessary.

E. Use of the Compositions of the Invention

The invention compositions are used in standard immuno or other binding assays in ways dictated by the nature of the specific reaction partner and the label, according to methods known in the art. Specific methodologies are illustrated below. These are meant for illustration only, and other specific compositions and other specific protocols which fall within the scope of the invention will be known to those in the art.

F. The Ferritin Assay

Ferritin is the major intracellular storage source of iron which can be mobilized as required and transported bound to the blood protein, transferrin. Apoferritin has a molecular weight of 440 kd and contains 24 protein subunits arranged as a spherical shell. When iron is bound under physiological conditions, ferritin consists of a heterogeneous population of molecules which contain 0-4500 iron atoms per entity. Ferritin is synthesized in the intestinal mucosa, liver, and spleen in response to dietary intake. Although most of the ferritin pool is intracellular, small but significant amounts are found in the blood, and increased serum ferritin levels have been related to the presence of certain diseases such as hepatic necrosis, malignancy, and severe inflammation. In the absence of these or other abnormal conditions, serum ferritin is secreted in constant proportion to the total iron stores. Quantitative determination of serum ferritin has thus become useful for monitoring iron storage levels in blood donors and in patients undergoing hemodialysis. Evaluation of serum ferritin levels also permits differentiation between iron-deficiency anemia and other forms of anemia.

Other assays for ferritin include radioimmunoassay (RIA) (Miles, L. E. M., et al, *Anal Biochem* (1974) 61:209; Luxen, A. W., et al, *Clin Chem* (1977) 23:683) and enzyme-linked immunosorbent assay (ELISA) (Watanabe, N., et al, *Clin Chem* (1979) 25:80; Conradie, J. D., et al, *S Afr Med J* (1980) 57:282). There have been no reported procedures for fluorescencelabeled immunoassay of ferritin, to Applicants' knowledge.

In conducting the assay, the biological sample is mixed with an antibody preparation reactive with ferritin and the labeled ferritin composition of the invention. Preferably this is done sequentially—i.e., the antibody preparation is mixed first with sample and, after incubation, with the labeled ferritin reagent of the invention. The invention composition effectively competes with the analyte ferritin for the anti-ferritin antibody; if the protocol is sequential, the sample ferritin will equilibrate with antibody before addition of competition. The immunocomplexes are then separated from the remainder of the sample by any of a number of protocols, including addition of an immunoprecipitant or by having provided the antibody on a solid support. The isolated immune complex is then dissolved to obtain a fluorescence reading or is read directly as a solid, or the fluorescence remaining in solution after separation of the complex is used as a measure of the ferritin in the sample.

G. IgE Assay

IgE is a class of immunoglobulin diagnostic for prediction of allergic reaction in children and in confirming suspected allergic diseases. Studies have shown that allergic conditions such as asthma, hay fever, and eczema result in IgE levels 3-10 times the normal level. Also, elevated serum IgE levels have been found in patients with parasitic disorders and in patients with certain types of cancer.

IgE has a molecular weight of approximately 196 kd and consists of two light chains and two heavy chains bound by disulfide bonds and noncovalent interactions. It can be quantitated in biological samples using RIA competitive binding (Johansson, S.G.O, *J Clin Path* (1968) 28 Suppl: 33) or by other solid-phase RIA techniques (Johansson, S.G.O., et al, *Immunol* (1968) 14:265; Hussain, R., et al, *Am J Trop Med Hyg* (1983) 32:1347), or by ELISA (Engvall et al, *Immunochem* (1971) 8:871). The procedure is conducted in a manner analogous to that set for for ferritin above except that the SRP in the composition is IgE rather than ferritin.

H. TSH Assay

Thyroid-stimulating hormone is a glycoprotein which stimulates the production of the thyroid hormones triiodothyronine (T3) and thyroxin (T4). TSH is secreted by the anterior lobe of the pituitary gland. Serum levels of TSH levels are indicative of hypothyroidism and hyperthyroidism because these are regulated in a feedback mechanism by the release of T3 and T4 by the thyroid gland. When thyroid levels are increased by hyperthyroidism, TSH secretion is inhibited, the converse is true when the T3 and T4 levels (associated with hypothyroidism) are low. The very low levels of TSH associated with hyperthyroid disease require a sensitive assay for their detection. Because of the sensitivity required in the assay, RIA procedures are available—for example, from Bio Rad and from Ventrex.

However, the use of radioisotopes has obvious disadvantages, and the fluorescent-labeled reagents of the invention provide the required sensitivity without the attendant problems.

One illustrative labeled reagent useful in this assay provided by the invention is that wherein the SRP is a purified anti-TSH antibody, and the binding agent is dextran. The assay can then be performed in a manner analogous to that for the commercially available RIA assays which involves contacting the sample to assayed with a solid support, such as a coated tube which is conjugated to or coated with specific anti-TSH antibody. The bound TSH is then detected by using the labeled reagent of the invention and the quantity of label is measured by fluorescence.

EXAMPLES

The following examples are meant to illustrate the invention and should not be construed to limit its scope.

Preparation A:

Preparation of 5-Fluoresceinyl thioureidoacetic Acid t-Butyl Ester

To a 50 ml round bottom flask equipped with magnetic stirring bar was added a solvent mixture (10 ml THF, 5 ml of $CHCl_3$, and 5 ml of DMF) and 168 mg (1 mmole) of glycine t-butyl ester hydrochloride. The solution was cooled by an ice-water bath and 415 ml (3 mmoles) of triethylamine was added. To the above mixture was added FITC (fluorescein isothiocyanate, 1 mmole, 385 mg) in small portions over 3 hours. The reaction mixture was allowed to stir overnight and then concentrated to a red-brown oil that was dissolved in 100 ml ethyl acetate and washed with 5 ml water followed by 2-10 ml portions of saturated brine. Preparative tlc on silica with 10% methanol in chloroform and a trace of acetic acid gave tlc pure material, 240 mg. Molar extinction coefficient: $\epsilon = 79,500$ $M^{-1}cm^{-1}$ ($\lambda max = 494$ nm) in 0.5M sodium carbonate, pH 9.53. Anal. calc for $C_{27}H_{24}N_2O_7S \cdot H_2O$: C, 60.22; H, 4.83; N, 5.20; S, 5.95. Found: C, 60.16; H, 4.85; N, 5.01; S, 6.15.

EXAMPLE 1

Preparation of Apoferritin Reagent

As described in detail below, the apoferritin reagent prepared in this example contains apoferritin surrounded by and covalently linked Fab' fragments which are labeled with fluorescein. The ratio of fluorescein/Fab' is 1.6. The ratio of Fab' groups to ferritin is 5.0.

Preparation of Apoferritin with a Multiplicity of Linker

Human liver ferritin was first reduced and dialyzed to remove iron and then reacted with N-ethylmaleimide (NEM) to inactivate sulfhydryl groups. 1.1 mg human liver ferritin in 0.36 ml buffer was dialyzed against $3 \times 300$ ml portions of 0.10M sodium acetate, 0.10M thioglycolate, pH 4.4, over 6 hr at room temperature, and dialysis then continued against $3 \times 300$ ml portions of 0.15M potassium chloride, and then followed by $3 \times 300$ ml portions 20 mM sodium phosphate, 1 mM EDTA, pH 6.0, with changes every 2 hr.

The dialysate, containing apoferritin (0.42 ml) was treated with NEM by adding, slowly with rapid stirring, 8.4 μl of 50 mM NEM in dimethylformamide (DMF). The resulting clear solution was incubated overnight at 25-30° C.

The solution was then adjusted to pH 7.0 by slow addition of 7 μl 0.50M sodium carbonate, pH 9.5. A solution of sulfo-SMCC (Pierce Chemical Co.), 5 μl, 35 mM in dry DMF, was added slowly with rapid stirring in an ice bath, and after addition was complete, the resulting solution was incubated at 30° C. for 90 min. Unbound NEM and sulfo-SMCC were removed by gel chromatography on a 1×10 cm Sephadex-G 25 column eluted with 0.1M sodium phosphate, 5 mM EDTA, pH 6.0. The protein-containing fractions were pooled and shown to contain linker to ferritin at a ratio of 8.0 by reacting a 200 μl aliquot with standardized mercaptoethanol solution and back-titrating of unreacted mercaptoethanol with 5,5'-dithiobis-(2-nitrobenzoic acid).

Preparation of Fluorescein Labeled Fab' Fragments

Rabbit F(ab')$_2$, available commercially or readily synthesized from rabbit IgG using pepsin digestion, was first converted to Fab' by treating with reducing agent. A 16 μ portion of 1.1M cysteamine hydrochloride solution was added in 3 equal portions to 1.6 ml of a solution containing 20 mg rabbit F(ab')$_2$ in 100 mM sodium phosphate, 5 mM EDTA, pH 6.0, with stirring over a 3 min period. The resulting clear solution was incubated at 37° C. for 2 hr and then dialyzed for 1 day against 6×100 ml buffer changes at 4° C. A 538 μl aliquot of the above solution was adjusted to pH 8.9 using an equal quantity of 0.5M sodium carbonate, pH 9.4, and the resulting solution put into a capped, argon-flushed vial with a magnetic stir bar. A freshly prepared solution of FITC (44.9 μl in 0.5M sodium carbonate, pH 9.4) was then added, and the resulting solution stirred for 77 min at room temperature in the dark. The reaction was stopped by the addition of about 3 mg solid glycine. The sample was then chromatographed on 0.7×18 cm Sephadex G-25 column prewashed with 1M propionic acid and equilibrated with pH 6.0 buffer. Fractions containing 3 drops each were collected, and fractions 25-39 containing labeled protein were pooled and dialyzed against pH 6.0 buffer to remove remaining glycine.

The resulting labeled Fab' fragments were shown to contain a fluorescein/Fab' ratio of 1.6 by ultraviolet spectroscopy. The Fab' thiol groups were also titrated with 5,5'-dithiobis(2-nitrobenzoic acid), and it was shown that 0.63 SH moieties per mole Fab' were present.

Completion of the Reagent

A 302 μl sample of the fluoresceinated Fab' prepared above, containing 14.0 nmoles thiol was added to 1.70 ml of the apoferritin conjugated to the multiple linker moieties prepared above. This provided 7.00 nmoles of bound linker. The reaction was allowed to run overnight (15 hr) at room temperature. A small amount of insoluble solid was removed by centrifugation, and the supernatant was applied to a 1×35 cm Ultrogel AcA 22 column to remove unbound fluoresceinated Fab'. The column was eluted with 50 mM sodium phosphate, 0.1% sodium azide, pH 7.5, and 8-drop fractions were collected. The fractions in the center of the first protein peak containing the desired complex were pooled.

The resulting complex was shown to contain 5.0 labeled Fab' fragments per ferritin by ultraviolet spectroscopy and BCA (Pierce Chemical Co.) protein analysis.

EXAMPLE 2

Preparation of IgE Reagent

The complex analogous to that in Example 1, but containing IgE as specific reaction partner, was prepared according to the procedure set forth in this example. The resulting complex contained 5.9 fluoresceinated Fab' moieties per IgE. The fluorescent labeling per Fab' fragment was approximately as in Example 1 (2.0 fluorescein/Fab' ).

Conjugation of IgE to Linker

A solution of 2.50 mg human IgE in 0.97 ml buffer was dialyzed against 4×1000 ml portions of 100 mM sodium phosphate, 5 mM EDTA, pH 6.0, over 2 days at 4° C. No blocking of thiol groups was necessary, as the IgE putatively contains no free sulfhydryl groups. Thus, the dialyzed IgE (0.89 ml) was treated with 21.3 μl of a 63 mM solution of sulfo-SMCC in dry DMF over 42 min with rapid stirring in an ice bath. The resulting clear solution was incubated at room temperature for 2 hr and unbound sulfo-SMCC removed by gel chromatography on 1×14 cm Sephadex G-25 columns eluted with 100 mM sodium phosphate, 5 mM EDTA, pH 6.0. The fractions at the center of the protein peak were pooled, and the number of bound linker moieties determined as described in Example 1. In this preparation, the resulting complex contained 8.6 moles linker/mole IgE.

Preparation of Labeled Reagent

The fluoresceinated Fab' fragment, prepared as in Example 1 but containing a ratio of fluorescein/Fab' of 2.0, was bound to the linker-conjugated IgE as follows. A 2.68 ml sample of fluoresceinated Fab' containing 202 nmoles thiol was added to 1.64 linker-conjugated IgE solution containing 65.6 nmoles linker and incubated for 4 days (90 hr) at room temperature. The small amount of insoluble material formed was removed by centrifugation and the supernatant was applied to a 1.5×50 cm Ultrogel AcA 34 column to remove unbound fluoresceinated Fab' . The column was then eluted with 100 mM sodium phosphate, 5 mM EDTA, pH 6.0, buffer. The central portions of the first protein peak were pooled and assayed for the number of fluoresceinated Fab' /IgE by ultraviolet spectroscopy and BCA protein analysis. This ratio was shown to be 5.9 labeled Fab' /IgE.

EXAMPLE 3

Relative Quantum Efficiency and Antigenic Reactivity of IgE Conjugates

The IgE compositions prepared in Example 2 containing a ratio of fluorescein/Fab' of 2.0 and Fab'/IgE of 5.9 were compared with respect to quantum efficiency and antigenic efficiency with IgE directly labeled by treating with FITC. The comparison FITC-treated IgE was shown by UV spectroscopy and BCA protein analysis to contain 10.3 fluorescein/IgE.

Solutions were made containing 1×10$^{-10}$M fluorophore of either the IgE directly labeled or the conjugate of Example 2. Fluorescence was read on a standard Immpulse ® fluorometer manufactured by Sclavo Inc. West Coast (Sunnyvale, Calif.) and compared to the fluorescence output of a model compound, 5-fluoresceinylthioureidoacetic acid t-butyl ester (Preparation A), which was given an arbitrary value of 1.0. The relative quantum efficiency on this scale for the directly labeled IgE, containing 10.3 fluorescein/IgE, was 0.587. The complex of the invention, containing a calculated value of 11.8 fluorescein/IgE, had a relative quantum efficiency of 0.901; almost twice as high.

In addition, the antigenicity of these materials was measured using IgE radioimmunoassay (Kallestad) and compared to the antigenic reactivity of unconjugated IgE, which was set at a value of 1.0. Both complexes lost antigenic reactivity, but the conjugate of the invention was 2.6 times as antigenic as the directly labeled fluorescein conjugate. The directly labeled IgE showed a relative antigenic activity of 0.144, while the composition of the invention has a relative antigenic reactivity of 0.371.

EXAMPLE 4

Preparation of Labeled T3 Reagent

The preparation of T3 also follows the general pattern of the foregoing examples. Conjugation of T3 to Linker To a solution of 3,3',5-triiodo-L-thyronine sodium salt (0.45 mmoles, 303 mg) in 10 ml of DMF and 70 $\mu$l of triethylamine (0.5 mmoles) under an argon blanket was added succinimidyl 4-(N-maleimidomethyl) cyclohexanel-carboxylate (SMCC, 0.5 mmoles, 167 mg) in portions over one hour. The reaction was allowed to stir for an additional four hours and the solvent was removed under reduced pressure. A solution of 10 ml of $H_2O$, 1 ml of saturated brine, and a few drops of 6N HCl, pH 3, was added to the residue, and it was extracted with 175 ml of ethyl acetate. The organic layer was washed by 2×20 ml portions of saturated brine and dried ($Na_2SO_4$). Removal of the solvent under reduced pressure gave an oil.

Purification by preparative tlc on silica ($CHCl_3$:MeOH:HOAc=80:20:trace) gave 67 mg of purified product. Recrystallization from ethyl acetate-cyclohexane gave 50 mg of pure T3-linker product—i.e., N-(4-(N'-maleimidomethyl cyclohexane-1-carboxyl) 3,3',5-triiodo-L-thyronine. Infrared and nuclear magnetic resonance spectra were consistent with the structure. Microanalysis for $C_{27}H_{25}N_2O_7I_3$: Calc.: C, 37.24; H, 2.87; N, 3.22; I, 43.78. Found: C, 38.05; H, 3.09; N, 3 14; I, 44.10.

Completion of Reagent

Fluoresceinated Fab' (fluorescein/Fab' =2.1), 10.6 mg, in 2.3 ml 100 mM phosphate, 5 mM EDTA, pH 6.0, buffer was placed in a vial and cooled in an ice-water bath. With good stirring, 100 ml of a dimethylformamide solution of N-(4-(N'-maleimidomethyl)cyclohexane-1-carboxyl) 3,3',5-triiodo-L-thyronine, 1 mg, was added over 67 minutes. The resulting mixture was stirred at room temperature for an additional hour. Reaction of an aliquot with 5,5'-dithiobis(2-nitrobenzoic acid) indicated that reaction was complete. The conjugate was purified to remove unbound T3 by passing it through a 2.4 cm×50 cm column of Ultrogel AcA 44 eluting with the same phosphate-EDTA buffer. Tubes from the central portion of the Fab' protein peak were pooled. The ratio of Fab' protein to T3 in this conjugate is 1:1.

EXAMPLE 5

Determination of Ferritin

Human serum samples were tested for ferritin. Results read on the Immpulse ® system. The assay employs the reagent prepared in Example 1. The procedure is calibrated using 4.0–50.0 ng/ml ferritin calibration standards. The assay as conducted using a manual batch procedure proceeds as follows in an illustrative determination.

Patient serum samples and calibrators, 20 $\mu$l each, were dispensed into tubes followed by 100 $\mu$l assay buffer wash using a Pipettor-Dilutor. Goat antiferritin antibody (1:100,000 dilution), 10 $\mu$l, was dispensed into the tubes followed by 50 $\mu$l assay buffer. The tubes were vortex mixed and incubated at 37° C. for 3 hours. The ferritin reagent of Example 1, 10 $\mu$l, was dispensed into the tubes followed by 50 $\mu$l of assay buffer. The tubes were vortex mixed and incubated at 37° C. for 30 minutes. Rabbit anti-goat Ig antibody (6:10 dilution), 10 $\mu$l, was dispensed into the tubes followed by 50 $\mu$l assay buffer wash. Polyethylene glycol solution (20%), 80 $\mu$l, was dispensed into the tubes followed by 420 $\mu$l assay buffer. The tubes were vortex mixed and incubated for 30 minutes at room temperature.

The tubes were centrifuged for 30 minutes to pellet the immune precipitate. The supernatant was decanted and measurement buffer, 500 $\mu$l, was added to dissolve the pellet, and the tubes were vortex mixed. The resulting solutions were aspirated into the flow cell of the Immpulse ® fluorometer and read.

A standard curve was calculated from the relative fluorescence intensities of the calibrators. The patient sample results are determined by comparison of their fluorescence values to the standard curve.

Figure 2B:
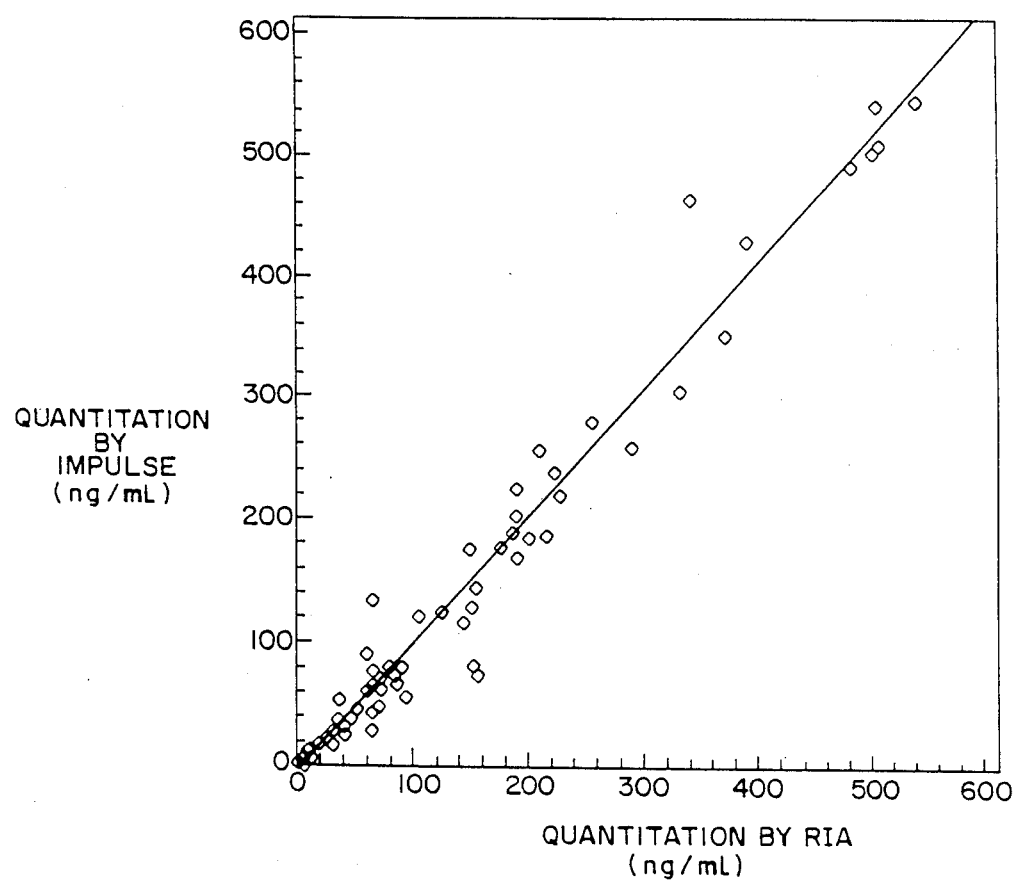
FIG. 2B shows the results of correlation of quantitation of ferritin using the method of the invention (y axis) with quantitation by RIA (x axis).

The results of the assay showing a plot of relative fluorescence intensity versus concentration in ng/ml is shown in FIG. 2A. A correlation of this study with RIA by standard methods marketed by Ramco Laboratories Inc. using 96 samples is shown in FIG. 2B. As shown in FIG. 2A, high levels of ferritin give reduced fluorescence, as the unlabeled ferritin becomes a more effective competitor. The correlation with quantitation by RIA is shown in FIG. 2B to be substantially linear.

EXAMPLE 6

Determination of IgE

In an analogous manner to that set forth above for ferritin, a manual batch procedure was conducted to determine IgE using 5.0 to 200 IU/ml calibration standards.

Patient serum samples and calibrators, 20 $\mu$l each, were dispensed into tubes followed by 100 $\mu$l assay buffer wash using a Pipettor-Dilutor. Fluorescent IgE reagent of Example 2, 10 $\mu$l, was dispensed into the tubes followed by 50 $\mu$l of assay buffer. The tubes were vortex mixed and then goat anti-IgE antibody (4:100,000 dilution), 10 $\mu$l, was dispensed into the tubes followed by 50 $\mu$l assay buffer wash. Polyethylene glycol solution (3.2%), 500 $\mu$l, was dispensed into the tubes followed by vortex mixing and incubating for 30 minutes at room temperature. The tubes were centrifuged for 30 minutes to pellet the immune precipitate. The supernatant was decanted and measurement buffer, 566 $\mu$l, was added to dissolve the pellet and the tubes vortex mixed. The resulting solutions were aspirated into the flow cell of the Immpulse ® fluorometer and read.

A standard curve is calculated from the relative fluorescence intensities of the calibrators. The patient sample results are determined by comparison of their fluorescence values to the standard curve.

Figure 3A:
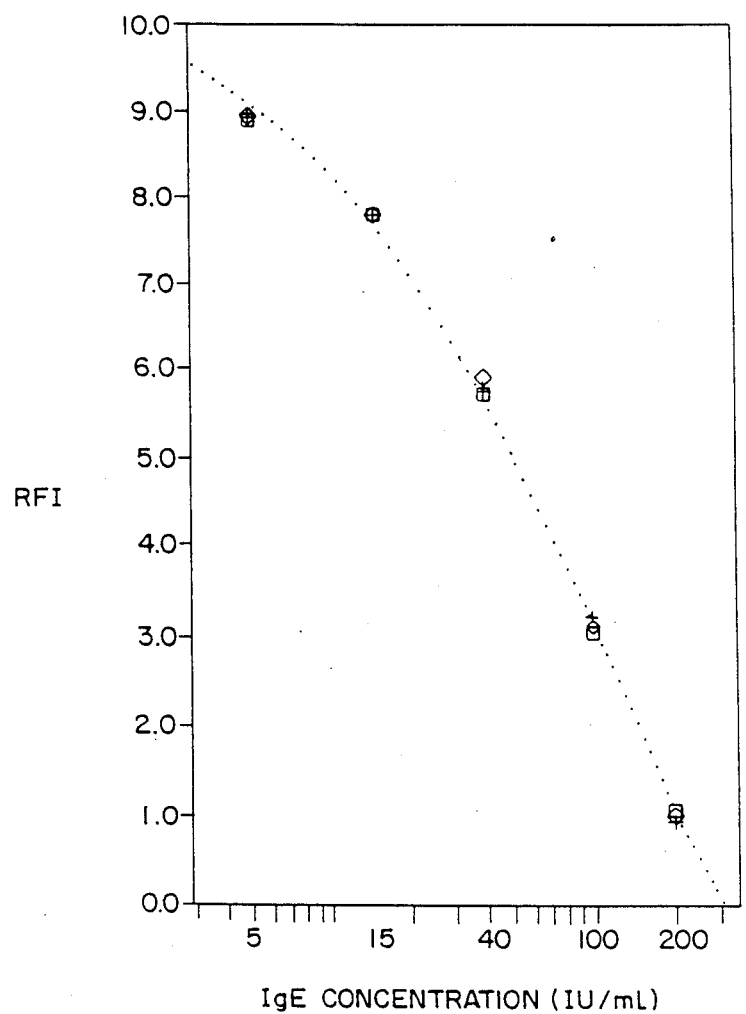
FIG. 3A shows the results of quantitation of IgE calibration standards using the method of the invention.
Figure 3B:
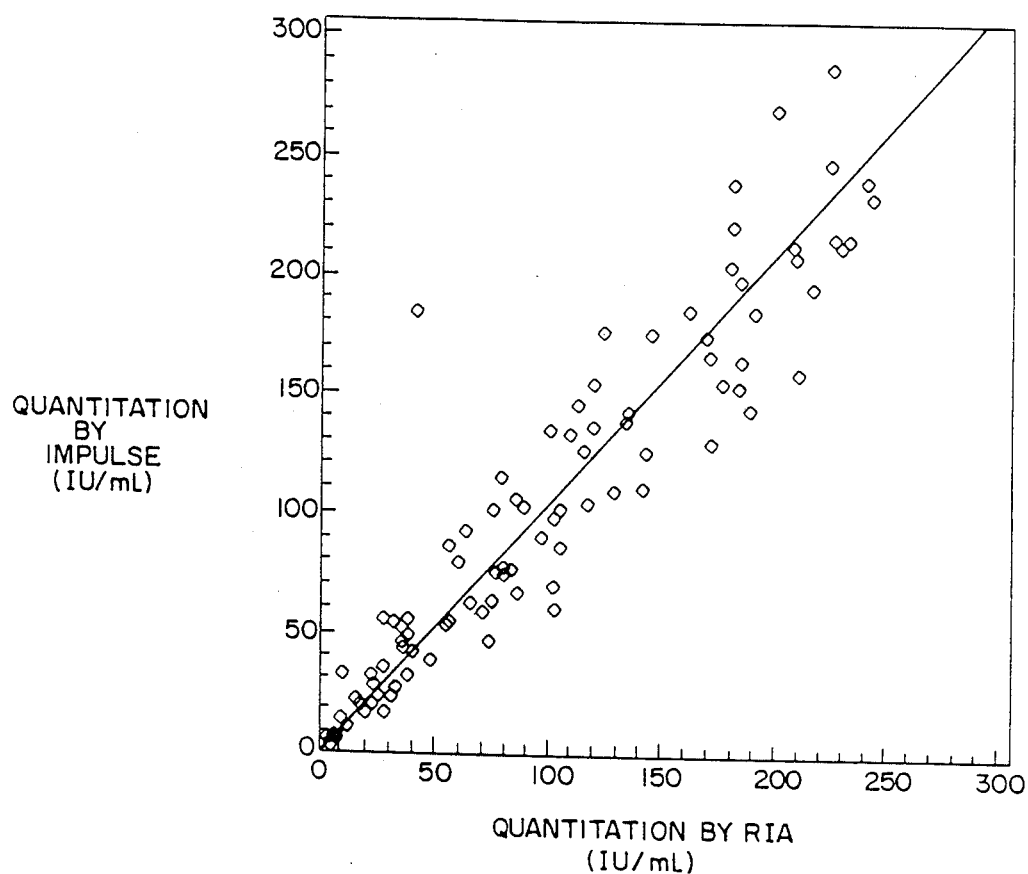
FIG. 3B shows the results of correlation of quantitation of IgE using the method of the invention (y axis) with quantitation by RIA (x axis).

Relative fluorescence intensity (RFI) results for the IgE calibration standards and correlation to RIA results for IgE patient samples are shown in FIGS. 3A and 3B.

EXAMPLE 7

Determination of T3

Twenty μl serum samples, calibrators and/or controls, 20 μl of anilinonaphthalene sulfonate (13.2 mg/ml) and 20 μl of goat anti-T3 antibody solution were added into 600 μl of assay buffer containing phosphate and bovine albumin. Into the above mixture, 20 μl of the reagent of Example 4 was added, mixed, and incubated for one hour at room temperature. One hundred μl of 20% polyethylene glycol solution was then added along with 20 μl of rabbit anti-goat Ig. The mixture was centrifuged, supernatant discarded, and the remaining pellet dissolved in 500 μl of measurement buffer, pH 11.8, and the relative fluorescence intensity (RFI) was obtained by the Immpulse ® Fluorometer. The calibration curve is plotted, RFI vs calibrator concentration, and the unknown quantitations are obtained through interpolation.

The table below shows the relation of fluorescence to concentration of standard calibrator for the reagent of the invention and directly labeled T3.

| Calibrator | Relative Fluorescence Intensity | |
|---|---|---|
| | FITC-T3 | FITC-Fab-SMCC-T3 |
| 0.2 | 4081 | 5551 |
| 0.5 | 3911 | 4954 |
| 1.0 | 3696 | 4526 |
| 2.0 | 3448 | 3906 |
| 6.0 | 3220 | 3219 |
| ΔRFI over assay range 0.2–6.0 ng/ml | 861 | 2332 |

It should be noted that at low concentrations of calibrator the assay using the labeled T3 of the invention is much more sensitive, and that the range of RFI is greatly expanded.

Example 8

Preparation of Derivatized Dextran

The intermediate, dextran monoamine, was prepared by adaptation of the method of Yalpani, M., et al, *J Polym Sci Polym Chem Ed* (1985) 23:1395 as follows: Dextran (Sigma, MW=73,400) (4.49 g, 0.0612 mmoles) was dissolved with gentle heating in 25 ml of deionized water contained in a 50 ml round-bottomed flask equipped with a magnetic stirring bar. Sodium chloride (2.74 g), ammonium acetate (689 mg, 8.95 mmoles) and sodium cyanoborohydride (640 mg, 10.2 mmoles) were added, a reflux condenser was attached, and the reaction was heated at 90° C. in an oil bath. After 118 hr, the solution was cooled to room temperature and added dropwise to 200 ml of ethanol. The liquid was decanted to leave a sticky white residue. This precipitate was redissolved in 20 ml of deionized water and placed in dialysis tubing (500 mm×31.8 mm, MW cutoff 6–8,000). Dialysis against 6 L of H$_2$O was performed for 42 hr with five changes. Precipitation of the dialysate from 600 ml ethanol/acetone (1:1) and drying of the resultant residue on an Abderhalden (methanol reflux) gave 2.74 g of a white powder. Titration of primary amine groups with 2,4,6-trinitrobenzene sulfonic acid ($\lambda$max=340 nm, $\epsilon_{340}$=1.05×10$^4$m$^{-1}$cm$^{-1}$) gave an amine to dry weight of dextran ratio of 0.76.

Dextran 3-(2-pyridyldithio)propionamide, was prepared from the above intermediate. In a 25 ml round-bottomed flask equipped with a magnetic stirring bar was added dextran monoamine (1.72 g, MW=73,400, 0.0235 mmoles), 4.95 ml of pH 7, 50 mM sodium phosphate buffer containing 2.5 mM EDTA, and 0.60 ml of pH 9.5, 0.5M sodium carbonate to obtain a reaction solution of pH 8.0. N-succinimidyl 3-(2-pyridyldithio)-propionate (Pierce, 98 mg, MW 312, 0.314 mmoles) in dimethylformamide (0.75 ml) was added and a white precipitate formed. Dimethylformamide, 1.00 ml, deionized water, 1.50 ml, and 1.80 ml pH 9.5, 0.5M sodium carbonate were added with stirring to give a homogeneous solution.

The reaction was allowed to proceed 18 hr at room temperature, then was adjusted to pH 6 with 1N HCl. Dropwise, 1.77 ml of a freshly prepared pH 6, 2.47M hydroxylamine solution (645 mg hydroxylamine hydrochloride, 15 mg EDTA, 1.5 ml deionized water, pH adjusted to pH 6 with 5N potassium hydroxide) was introduced. The reaction was stirred an additional 1 hr and placed in dialysis tubing (50mm×31.8 mm, MW cutoff 6–8,000). Dialysis was performed against 6 L of deionized water for 76 hr with nine changes.

Concentration of dialysate, and drying in an Abderhalden (at methanol reflux) yielded 1.47 g of white powder. Titration of 2-thiopyridone ($\lambda$max=343 nm, $\lambda_{343}$=8.08×10$^3$) via dithioerythritol cleavage of the 2-thiopyridyl moieties gave a thiopyridyl to dry weight dextran ratio of 0.90.

EXAMPLE 9

Preparation of Fluorescein-Labeled Derivatized Dextran

In a 10 ml round-bottomed flask equipped with a stirring bar was added dextran 3-(2-pyridyldithio) propionamide (MW=73,400, 189 mg, 2.58 μmoles) and 1.90 ml of dry dimethylsulfoxide. Gentle heating was required to dissolve the dextran. Pyridine (58 μ, 725 μmoles) and tresyl chloride (Fluka Chemical Corp., 31 μl, 281 μmoles) were added with stirring and the reaction was placed under an argon atmosphere.

After 6.5 hr, the tresyl substituted dextran solution was added dropwise to a 25 ml round-bottomed flask containing a freshly prepared solution of 5-(2-mercaptoacetamido)fluorescein flourescein (0.514 mM in 1.44 ml pH 7, 100 mM phosphate containing 5 mM ETDA and 1.44 ml, pH 9.5 0.5M carbonate). The reaction flask was washed with an additional 0.50 ml of dimethylsulfoxide, and the wash was added to the aqueous reaction mixture, and resulting solution stirred at room temperature. After 15 hr, 2 ml of 0.5M carbonate (pH 9.5) was added. The red reaction mixture was stirred an additional 1 hr and centrifuged to remove insoluble particulates. Two portions, 3 ml each, of the resulting red aqueous supernatant were added dropwise to 2×15 ml centrifuge tubes containing 10 ml of ethanol acidified with two drops 6N HCl. The precipitate was collected by centrifugation and the process repeated five times in the same tubes until all of the aqueous supernatant, 30 ml, had been precipitated. The two dextran containing pellets were combined after redissolving in hot water (1 ml each). The dextran was reprecipitated from 12 ml of ethanol (acidified with 2 drops of 6N HCl) in a 15 ml centrifuge tube. The precipitation process was repeated until ≳98% non-dextran bound fluorescein was removed (approximately 15 precipitations). Product purity was monitored via TLC with Whatman reverse phase MKC$_{18}$F plates (solvent system: CH$_3$OH/H$_2$O (8:2); unbound fluorescein migrated with the solvent front, dextranbound fluorescein remained at the origin).

Purified product was taken up in 4 ml of water and placed in dialysis tubing (10 mm×6.4 mm, 12–14 MW cutoff). Dialysis against 6 l of deionized water over 68 hr was performed with seven changes. The dialysate was concentrated and dried in vacuo to yield 114 mg of fluorescein-bound derivatized dextran. By UV determination (pH 9.5, 0.5M carbonate; λmax=494 nm, ε$_{494}$=75,000), the fluorescein to dry weight dextran (MW=73,400) ratio was 6.58.

3-mercaptopropionamide of fluorescein-labeled dextran was prepared from 3-(2-pyridyl dithio)propionamide of fluorescein-labeled dextran with reaction with dithioerythritol as follows: In a 1 dram vial was placed, purified fluorescein-labeled derivatized dextran conjugate (37 mg, MW=75,000), 646 μl of a degassed solution of pH 6, 100 mM phosphate containing 5 mM EDTA, 161 μl carbitol, and dithioerythritol, 113 μl, 13 mM in the same degassed buffer as above. This solution was applied to an Ultrogel AcA22 column (column volume=85 ml) and eluted with degassed pH 6, 100 mM phosphate, 5 mM EDTA (1 drop/25 sec; 35 drops/tube). Tubes 35 and 36 (Fraction A) were pooled and tubes 37–41 (Fraction B) were pooled.

Fraction A was placed in dialysis tubing (10 mm×6.4 mm, 12–14 K, MW cutoff) and dialyzed against 6 L of deionized water for 112 hr with seven changes of the supernatant. The dialysate was then concentrated and dried in vacuo. UV determination (pH 11.9 30 mM phosphate; λmax=494, ε$_{494}$=75,000 gave a fluorescein to dry weight dextran (MW=75,000) ratio of 6.84.

Fraction B was concentrated in vacuo to 800 μl, dithioerythritol (114 μb, 5 mM in degassed pH 6, 100 mM, phosphate 5 mM EDTA) was added, and the solution was placed in dialysis tubing (10 mm×6.4 mm, 12–14K MW cutoff). Dialysis against 100 ml of pH 6 100 mM phosphate, 5 mM EDTA (degassed) was performed over 113 hr with six changes. The resultant dextran concentration was determined by UV at 494 nM to be 10.68 mg/ml (pH 11.9, 30 mM phosphate; assuming a fluorescein to dextran ratio=6.84). The thiol content by 5,5'-dithiobis(2-nitrobenzoic acid) titration (pH 8.6, 0.4M tris buffer) gave a thiol to dextran ratio of 0.96.

EXAMPLE 10

Conjugation of Fluorescein Labeled Dextran with Goat Anti-TSH Antibody

Purified goat anti-TSH antibody, 1.00 ml, was dialyzed against 4×800 ml 100 mM sodium phosphate, 5 mM EDTA, pH 6.0. Sulfo-SMCC, 2.05 mg, 4.70 μmole, Pierce Chemical Co. was dissolved in 75 μl dry dimethylformamide. Sulfo-SMCC, 21.9 μl, was slowly added to 0.72 ml dialyzed antibody solution with stirring on ice. After the addition was completed, the solution was warmed to room temperature and incubated for 2 hr.

Unreacted Sulfo-SMCC was separated from the antibody by chromatography on Sephadex G-25 (1×14 cm column equilibrated with 50 mM sodium phosphate, 2.5 mM EDTA, pH 7.0).

The number of bound SMCC crosslinkers per antibody was determined by reacting 96 μl of the pooled protein fractions with 1.0 μl 3.5 mM mercaptoethanol diluted with buffer to a total volume of 201 μl. After incubation for 30 min at 37° C., 100 μl 0.75 M Tris-HCl, pH 8.8 was added and the amount of remaining thiol was determined by addition of 2.0 μl 2.5 mM Ellman's Reagent, 5,5'-dithiobis(2-nitrobenzoic acid).

Fluorescein-dextran conjugate, 300 μl, (36 nmole thiol residue) was added to 1.42 ml antibody solution (16.8 nmole crosslinker residues). The resulting solution was allowed to react for 6 days at room temperature.

Unreacted crosslinker was capped with 1.0 μl 35 mM mercaptoethanol to react with any remaining maleimide functions. Unbound fluorescein-dextran was separated from the fluorescein-dextran-antibody conjugate by gel chromatography on Ultrogel AcA 22 column (1.5×50 cm, 50 mM sodium phosphate, 2.5 mM EDTA, pH 7.0 buffer). The ratio of labeled dextran to antibody in the product was at least 1:1 but not more than about 9:1.

EXAMPLE 11

Thyroid Stimulating Hormone (TSH) Assay Employing Fluorescein-Dextran-Anti-TSH Conjugate TSH calibrators and patient samples, 200 μl each, are added to 12×75 mm polystyrene plastic tubes coated with adsorbed antibody to TSH. The tubes are covered and incubated overnight at 37° C. The supernatant is decanted and the tubes washed with two 2.0 ml portions of phosphate buffered saline. Fluorescein-dextran-anti-TSH conjugate, 200 μl, is added to each tube and the tubes incubated one hour at 37° C. The supernatant is decanted and the tubes washed with two 2.0 ml portions of assay buffer. Measurement buffer, 566 μl, is added to the tubes and they are incubated one hour at 37° C. The fluorescence of the contents of each tube is read on the IMMPULSE ® Fluorometer (Sclavo, Inc.). TSH concentration results are calculated by interpolation from a standard curve constructed from the fluorescence readings of the calibrators.

We claim:

1. A method to convert hydroxyl groups of derivatized or protected dextran to groups displaceable by a nucleophile which comprises treating a solution of derivatized or protected dextran in dry DMSO with a solution of tresyl chloride and pyridine.

2. A method to label dextran which comprises contacting tresylated dextran or tresylated derivitized or protected dextran in solution resulting from the preparation of said tresylated dextran by a method which comprises treating said dextran in dry DMSO with a solution of tresyl chloride and pyridine with a label having a nucleophilic functional group for time sufficient to displace the tresyl groups with label.

* * * * *